US00PP12350P2

(12) United States Plant Patent
Swartz et al.

(10) Patent No.: US PP12,350 P2
(45) Date of Patent: Jan. 15, 2002

(54) RASPBERRY PLANT NAMED 'EMILY'

(75) Inventors: Harry Jan Swartz, Laurel, MD (US); Joseph A. Fiola, Whiting, NJ (US); Herbert D. Stiles, Blackstone, VA (US); Brian R. Smith, River Falls, WI (US)

(73) Assignees: University of Maryland, College Park, MD (US); Virginia Tech Intellectual Properties, Inc., Blacksburg, VA (US); University of Wisconsin at River Falls, River Falls, WI (US)

( * ) Notice: Subject to any disclaimer, the term of this patent is extended or adjusted under 35 U.S.C. 154(b) by 0 days.

(21) Appl. No.: 09/177,126

(22) Filed: Oct. 22, 1998

(51) Int. Cl.[7] ..... A01H 5/00
(52) U.S. Cl. ..... Plt./204
(58) Field of Search ..... Plt./204

(56) References Cited

U.S. PATENT DOCUMENTS

PP6,597 P * 2/1989 Keep ..... Plt./204
PP7,067 P * 12/1989 Sanford et al. ..... Plt./204
PP9,477 P * 3/1996 McGregor ..... Plt./204

* cited by examiner

*Primary Examiner*—Bruce R. Campell
*Assistant Examiner*—Wendy C Baker

(57) ABSTRACT

The present invention is a new and distinct spring bearing red raspberry cultivar named 'Emily', which is capable of producing highly cohesive and firm fruit in the spring midseason, the fruit being larger and more durable than that of the standard cultivars. The cultivar is characterized by moderate suckering ability, small red thorns and its large and elongate fruit which have a much narrower cavity than standard cultivars. Because of this trait, the fruit of 'Emily' is structurally more sound than other cultivars.

6 Drawing Sheets

FIELD OF THE INVENTION

This invention concerns a new and distinct cultivar of raspberry plant with a botanical name of *Rubus ideaus L.*

DESCRIPTION OF RELATED PRIOR ART

Several cultivars of raspberry plant are known. For instance, raspberry cultivars named 'Anne', 'Caroline' and 'Lauren' have been described in U.S. Plant Pat. No. 10,411, 10,412 and 10,610, respectively. The new and distinct cultivar of the present invention is a raspberry plant named 'Emily'. This new and distinct cultivar of the present invention differs from 'Anne' in bearing red fruit in the spring, rather than golden fruit in the fall. 'Emily' can be distinguished from 'Caroline' in that 'Emily' is spring bearing, but 'Caroline' is fall bearing. 'Emily' and 'Lauren' are both spring bearing red raspberry cultivars, but 'Emily' can be distinguished from 'Lauren' in having a later ripeness period.

ORIGIN OF THE NEW CULTIVAR

The new cultivar of spring bearing red raspberry originated from a controlled cross at the University of Maryland Greenhouses in College Park, Md. The cross "AM" was 'CDA-2' (unpatented)×'Glen Moy' (unpatented) and was made in the winter of 1989. CDA-2 (unpatented) was a selection of the cross 'Southland' (unpatented)× 'Williamette' (unpatented), made in 1982. This year was designated "J" as part of the University of Maryland at College Park; Rutgers University of New Brunswick, N.J.; Virgina Polytechnic Institute and State University, Southern Piedmont Agricultural Research and Education Center at Blackstone; and the University of Wisconsin at River Falls cooperative breeding program. The clone was first selected in 1992 at the Wye Research and Education Center of the University of Maryland located at Centerville, Md. and was therefore designated "–1". Thus, the complete breeding designation was "JAM-1".

SUMMARY OF THE NEW CULTIVAR

This application relates to a new and distinct red fruited, spring bearing raspberry cultivar, botanically known as *Rubus ideaus L.* . The following characteristics are outstanding:

1. Production of fruit which are more durable than the standard cultivars in use, primarily due to its narrow cavity, firm flesh, thick drupelets and elongate conic shape.
2. Production of fruit which is larger and more flavorful than mid-season spring bearing cultivars adapted to the mid-Atlantic states.

The following characteristics are useful in distinguishing this cultivar and can be useful for cultivar indetification.

1. Plants are moderately suckering and very upright, growing to 4 feet or taller when mature. Canes are only moderately cold hardy, i.e. not recommended for areas where the minimum winter temperature is less than 0° F.
2. Canes have only a moderate amount of small thorns.
3. Leaves have a relatively longer petiolule in relation to leaf size than most cultivars.
4. The fruit has a very narrow cavity, very cohesive, red and very symmetrical. Fruit can be stacked several high before the fruit cavity is collapsed on the lower fruit. The fruit has an even collar and a good flavor.
5. The fruit is produced in the midseason from the floricanes. Primocane produced fruit is unusual.

BRIEF DESCRIPTION OF THE PHOTOGRAPHS

The accompanying photographs show typical characteristics of the new variety:

DESCRIPTION OF THE NEW CULTIVAR

Figure 1:
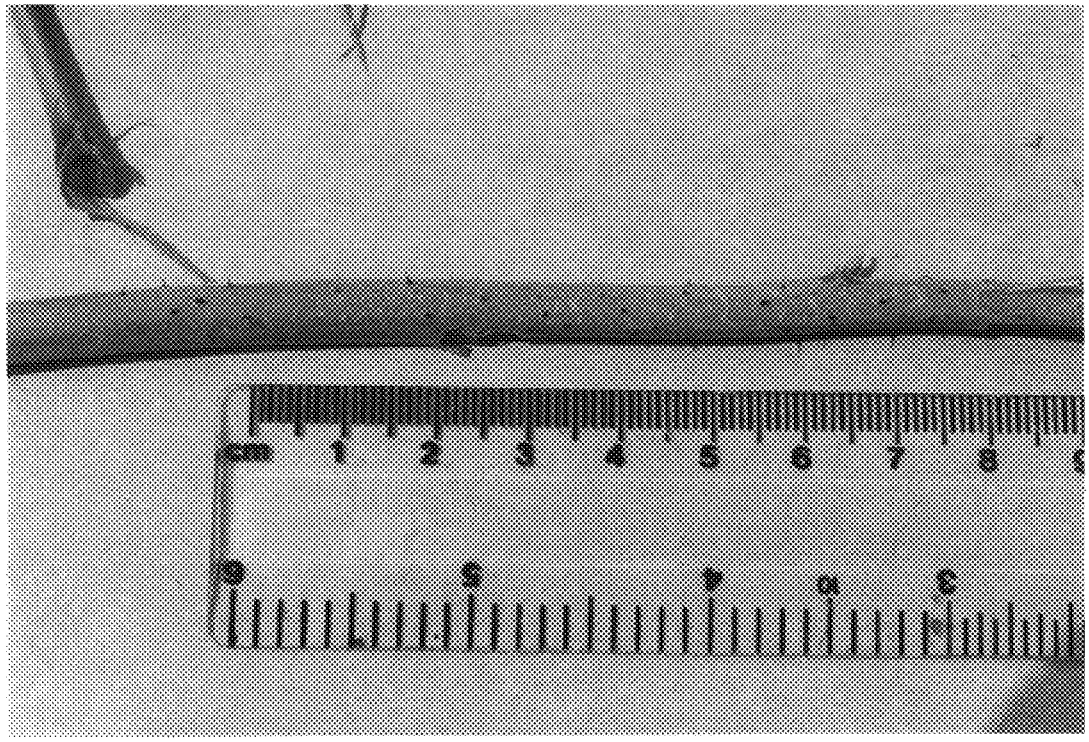
FIG. 1 shows the type and density of thorns on an 'Emily' primocane.
Figure 2:
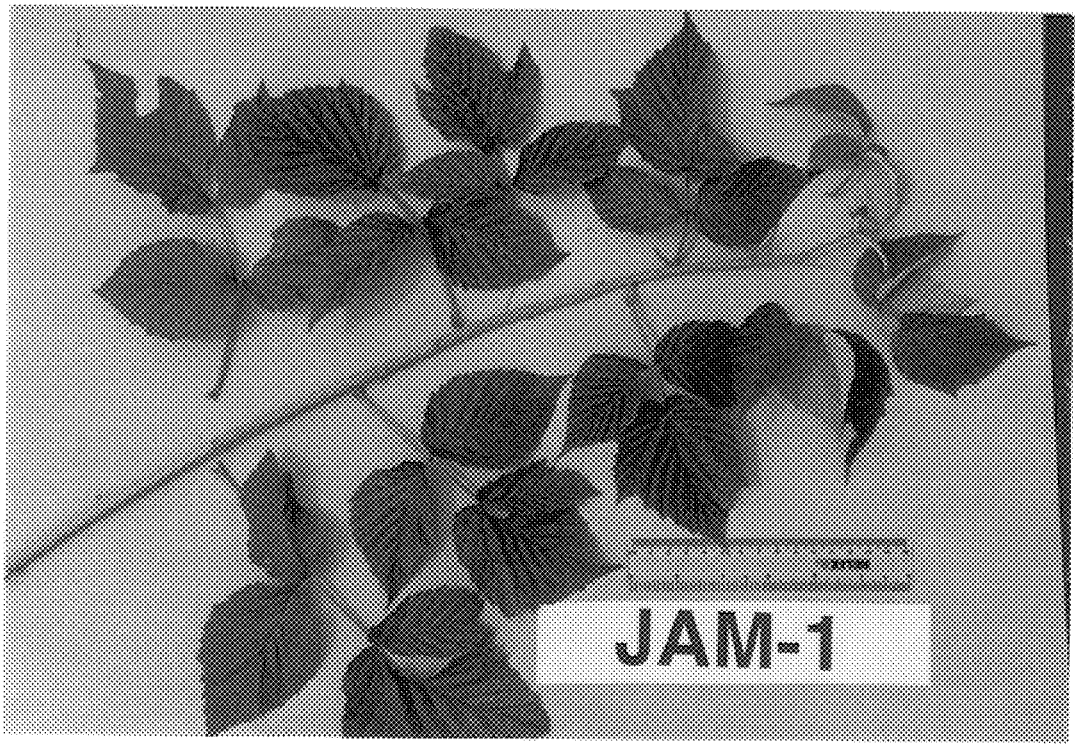
FIG. 2 shows a close-up coloring and size of 'Emily' leaves and their long petiolule, the ruler is 6 inches long.
Figure 3:
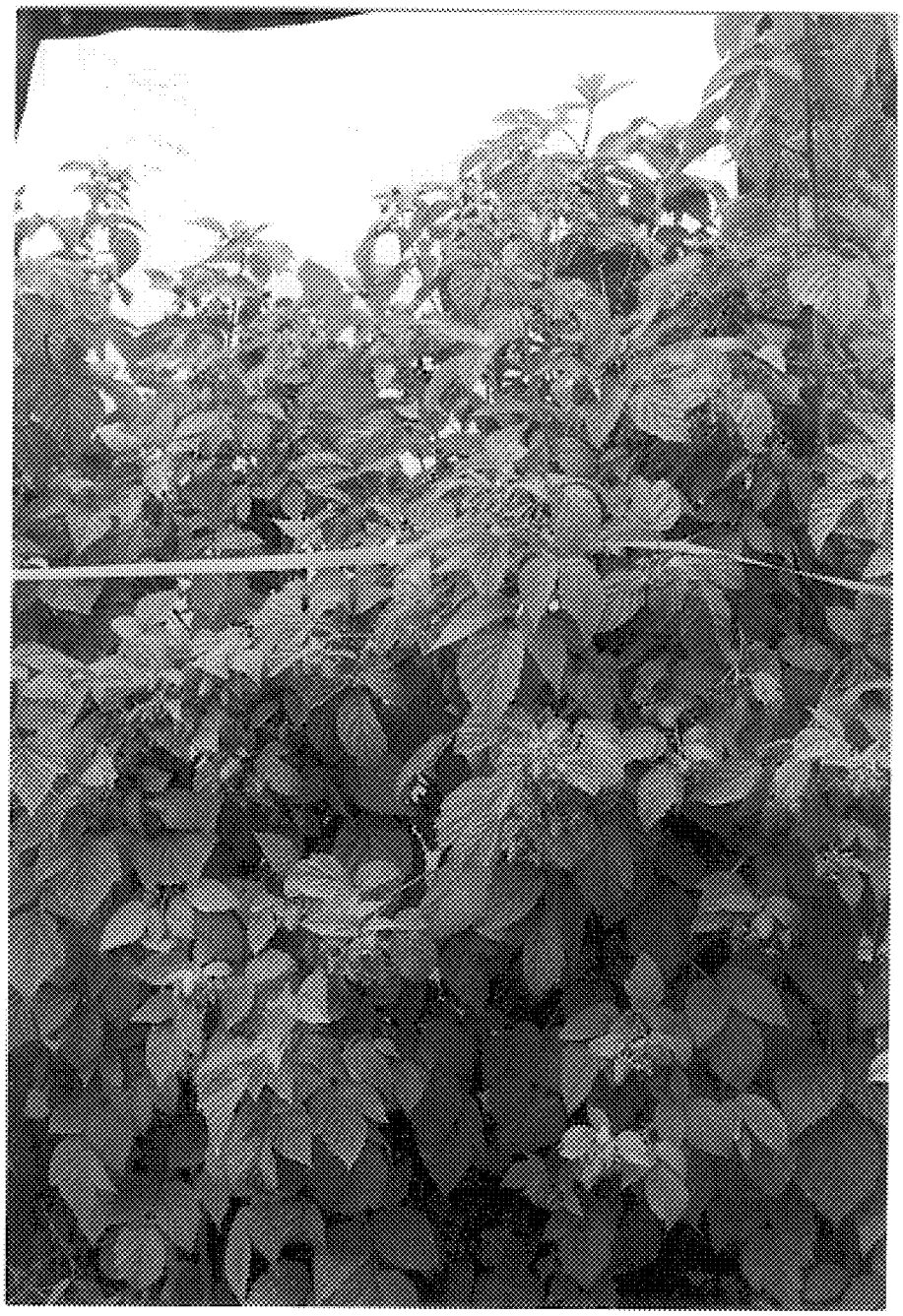
FIG. 3 shows an 'Emily' plant in fruit in June 1997, the tape is at 3 feet height, the plants are in their second growing season in Millersville, Pa.

The following is a detailed description of the new cultivar, including fruit production, together with the cultivar's morphological characteristics. The characteristics of the cultivar were compared other standards used in the Mid-Atlantic Region of the U.S. The description is based on information provided by cooperating scientists from plants grown in fields at Cream Ridge N.J., Millersville, Pa., and S. Deerfield, Mass., and from plants grown in the greenhouses at College Park, Md. 'Emily' produces a moderate number of root-and crown-suckers; on average, 43 suckers per 10 ft. of row were counted on 5 year old plants in Colt's Neck N.J. This number is similar to 'Lauren' (U.S. Plant Pat. No. 10,610), 'Tulameen' (unpatented) and 'Sentry' (unpatented), but greater than 'Titan' (U.S. Plant Pat. No. 5,404) and 'AmosH' (unpatented), typical cultivars tested or grown in the eastern United States. During the growing season, primocanes are light green colored (Royal Horticultural Society plate 145A) with a light red blush (Royal Horticultural Society plate 59B) in full sun, usually unbranched, erect to arching and moderately vigorous. Floricanes are moderately exfoliating at their base, not exfoliating at their apex and dark brown in color throughout their length (Royal Horticultural Society plate 175A). Thorns are moderate in density, 1 mm to 2 mm in length, stout and dark red (Royal Horticultural Society plate 59A) at the base, but lighter in color (Royal Horticultural Society plate 59B to Royal Horticultural Society plate 59C) and thinner at their apex (see FIGS. 1 and 2). The red coloration extends another 0.5 mm into the surrounding cane. Leaf upper surfaces are dark green, most closely in hue to Royal Horticultural Society Color Plate 137A, while the lower surface of the leaf is pubescent giving this surface a greyer color (Royal Horticultural Society plate 194B). Leaves are trifoliolate to pentafoliolate and average 12 cm from the distal end of the petiole to the distal end of the terminal leaflet (see FIG. 3). The cultivar has a slightly longer than average petiolule between the basal leaflets and more distal leaflet. Petiole color is light green (Royal Horticultural Society plate 145A). The basal leaflets average 12 cm from terminal point to point. Leaf serration is common for most cultivars of red raspberry and cannot be used to distinguish this cultivar.

Figure 4:
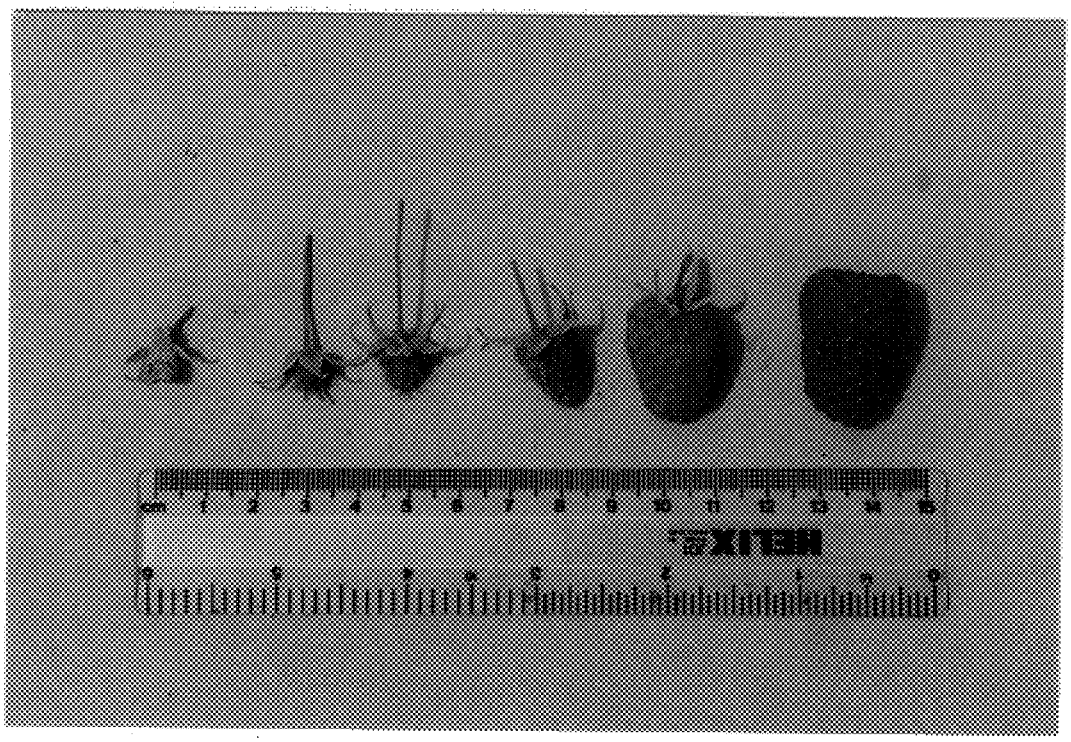
FIG. 4 shows development of 'Emily' flowers and fruit.
Figure 5:
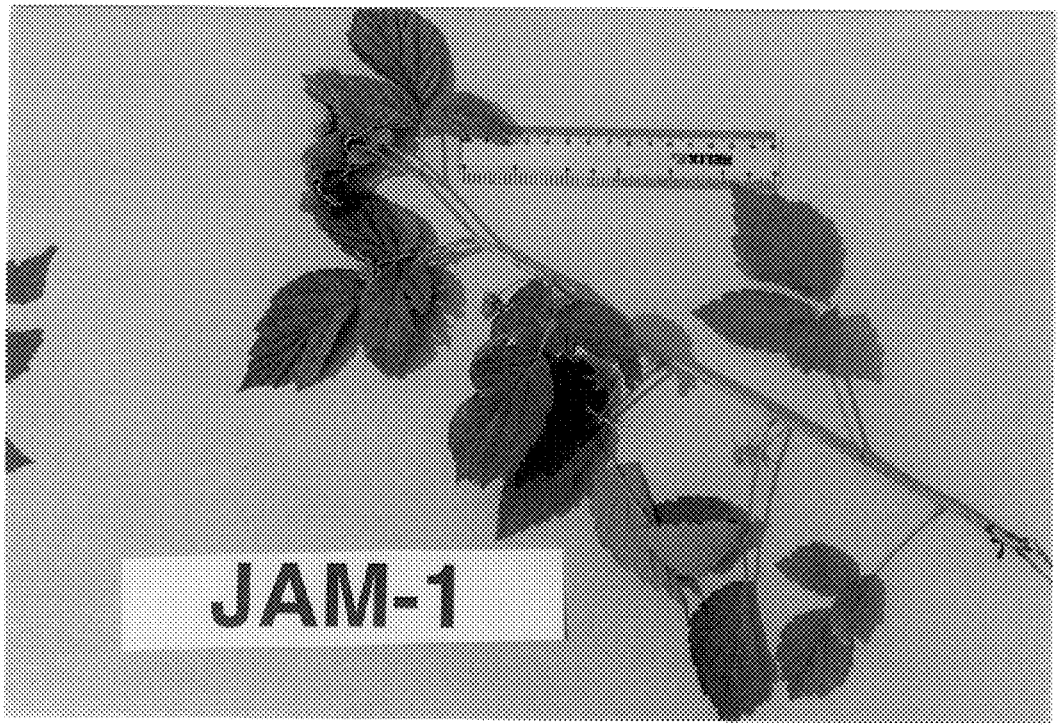
FIG. 5 shows a fruiting cluster of 'Emily', showing the exposure of the fruit.
Figure 6:
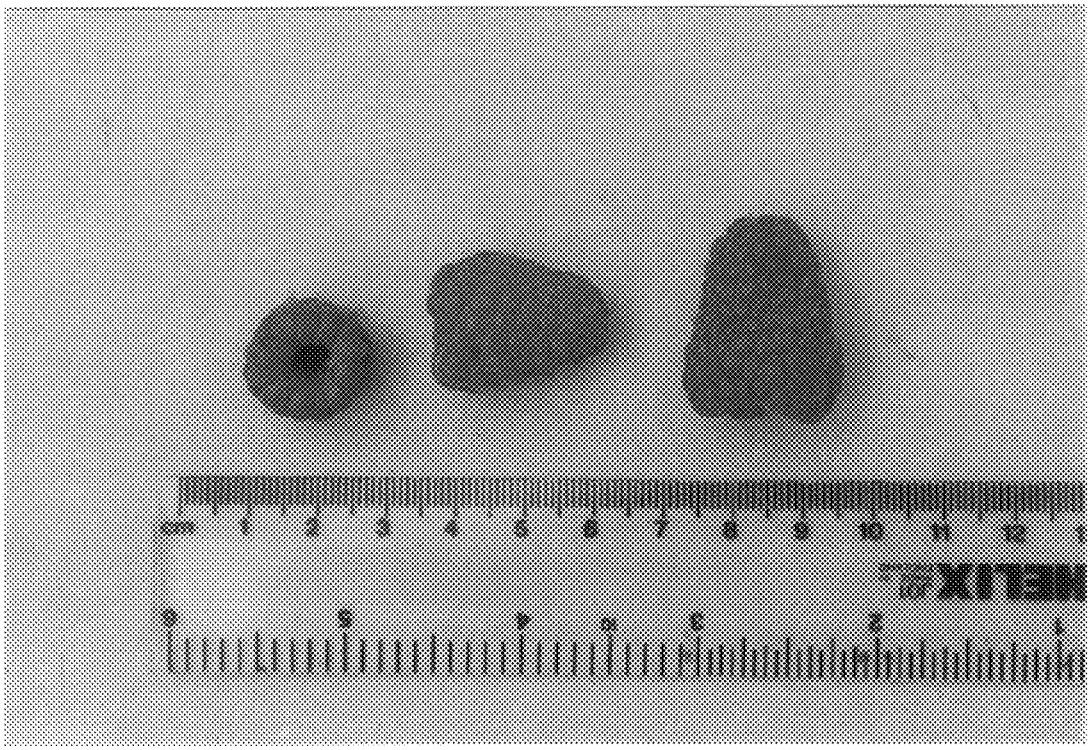
FIG. 6 shows the size, uniformity, shape and narrowness of cavity of harvested 'Emily' fruit.

Fall fruit is only very occasionally borne on the top of the primocanes. Floricanes suffer cold injury in mid winter if temperatures fall below 0° F. or if a warm spring is interrupted by an unusual period of freezing temperatures. This pattern of early growth initiation, and from its behavior in the winter in the greenhouse, indicates that 'Emily' has a slightly shorter chilling requirement than most eastern United States cultivars. Canes can flower from all live buds in April to May depending on latitude, and fruit from mid June to late July in the eastern U.S. This ripeness period is 1–2 weeks later than 'Lauren' (U.S. Plant Pat. No. 10,610) and 'Reveille' (unpatented), but overlaps 'Titan' (U.S. Plant Pat. No. 5,404). Flower morphology and early fruit morphology is typical of most red raspberry cultivars (unscented, 5 white petals 0.6 cm long resembling Royal Horticultural Society plate 155D; 5 sepals resembling Royal Horticultural Society plate 194B and 1.1 cm long) and cannot be used to identify 'Emily' (see FIG. 4). Flower petals are not persistant. The ring of anthers, when erect, are usually 0.7 cm in diameter, this number increases over time. Fruit trusses are typical cymose clusters with 6 to over 30 fruit well spaced out on a truss axis (see FIG. 5). After 25 days after pollination, fruit is easily distinguishable for this variety. It is moderately red when ripe, both externally and internally, closely resembling Royal Horticultural Society color plate No. 46A (see FIG. 6). Fruit has a slight pubescence, producing a slightly dull glossy appearance. Fruit is decidedly conic, very large and symmetrical. Primary fruit averages 3 cm in length and 2.3 cm in width at the shoulder, producing a 4 to 3 length to width ratio. Drupelets are held together tightly. The collar is very uniform, commonly lacking a notch. The primary fruit cavity width is smaller than almost all large-fruited cultivars, averaging 0.8 cm diameter, and represents 40% of the thickness of the fruit at its widest diameter. The cavity narrows significantly and is relatively acute (pointed) at its terminus inside the fruit. The drupelet thickness is higher than most cultivars (see FIG. 6). This combination of traits, with the very good firmness of 'Emily' flesh, accounts for the superior durability of 'Emily' fruit. The fruit readily separates from the plant's recepticle, even when slightly unripe. The plant does not break down after at least one week in common storage at 40° F. Flavor is mild to sweet and characteristic of red raspberry.

The plant is field resistant to many of the common pests and diseases in the eastern United States, e.g. mildew and verticillium wilt. The plant's reaction to *Phytophthora fragarae* root rot and late leaf rust is moderately susceptible, based on field reaction, not in controlled testing. Fruit is usually free from rot in the field.

FRUIT PRODUCTION

'Emily' has been tested in a grower trial in Millersville, Pa. The following data were collected in the summer and fall of 1997, the first year of production. Mid winter temperatures were below 0° F. on several occasions in the winter of 1996–1997. In this test, percent canes alive are the number of canes surviving winter with at least 25 inches of lateral bud break.

TABLE 1

Comparison of fresh fruit characteristics of 'Emily'

| | Yield in lbs/acre | Fruit Weight (grams) | Percent Canes Alive |
|---|---|---|---|
| Emily | 4470 | 3.5 | 47 |
| Lauren | 6049 | 3.0 | 82 |
| Sentry | 2678 | 2.2 | 47 |
| Tulameen | 339 | 4.5 | 12 |

'Emily' has been asexually reproduced in S. Deerfield, Mass. and College Park, Md. since 1994 by meristem-originated tissue culture using branching for multiplication as forced by the addition of 3 to 15 micromolar benzyl adenine to the medium. 'Emily' has also be produced by field suckering since 1994. Plant production occurred at S. Deerfield, Mass. and College Park, Md. Over that period, no off-type of 'Emily' has been observed or reported to us and it is stable.

What is claimed is:

1. A new and distinct spring bearing red raspberry plant known as 'Emily' as described herein, illustrated and identified by the characteristics set forth above.

* * * * *